United States Patent [19]
Hirschauer et al.

[11] Patent Number: 6,028,024
[45] Date of Patent: Feb. 22, 2000

[54] CATALYTIC COMPOSITION AND ALIPHATIC HYDROCARBON ALKYLATION PROCESS

[75] Inventors: André Hirschauer, Montesson; Hélène Olivier-Bourbigou, Rueil Malmaison, both of France

[73] Assignee: Institut Francais du Petrole, Rueil Malmaison, France

[21] Appl. No.: 09/055,886

[22] Filed: Apr. 7, 1998

[30] Foreign Application Priority Data

Apr. 8, 1997 [FR] France .................................. 97 04381

[51] Int. Cl.⁷ ...................................................... C08F 31/00
[52] U.S. Cl. .............................................................. 502/162
[58] Field of Search .................................... 502/162, 164, 502/167, 200

[56] References Cited

U.S. PATENT DOCUMENTS 5,750,455  5/1998  Chauvin et al. ...................... 502/164

FOREIGN PATENT DOCUMENTS 0 576 323  12/1993  European Pat. Off. .
0 709 356   5/1996  European Pat. Off. .
   960086   6/1964  United Kingdom .

*Primary Examiner*—Elizabeth D. Wood
*Attorney, Agent, or Firm*—Millen, White, Zelano & Branigan, P.C.

[57] ABSTRACT

The invention concerns a catalytic composition resulting from a mixture of at least one aluminium halide, at least one quaternary ammonium halide and/or at least one amine hydrohalide and at least one group IVB metal compound, preferably a group IVB metal halide. The invention also concerns a process for alkylating isoparaffins by olefins using that composition, the olefin preferably being a low reactivity olefin.

15 Claims, No Drawings

CATALYTIC COMPOSITION AND ALIPHATIC HYDROCARBON ALKYLATION PROCESS

FIELD OF THE INVENTION

The present invention relates to a catalytic composition, generally ionic and at least partially liquid, and to a process using that composition for the production of paraffinic hydrocarbons by addition of at least one olefin, preferably a low reactivity olefin such as ethylene, to at least one isoparaffin.

BACKGROUND OF THE INVENTION

A large number of acidic, liquid or solid catalysts are known for carrying out alkylation of isoparaffins such as isobutane and/or isopentane, using olefins such as propylene, 1-butenes and 2-butenes and isobutene. Industrially, the most frequently used catalysts are concentrated sulphuric acid and hydrofluoric acid, used alone or mixed with Lewis acids such as boron trifluoride. Using hydrofluoric acid in such processes is a problem because of its toxicity and high volatility. The use of sulphuric acid in such processes causes a problem due to high consumption of the catalyst necessitating expensive re-treatment. For this reason, the use of solid catalysts or catalysts which are supported on solids such as aluminosilicates or metal oxides such as zirconia treated with sulphuric acid has been recommended. However, solid catalysts have been proved to have low selectivity and low activity. Such catalysts are of particularly low activity with low reactivity olefins such as ethylene. Further, the catalysts usually used in industry react with ethylene to form stable esters. The use of aluminium chloride has been studied and proposed.

French patent application FR-A-2 626 572 and European patent application EP-A-0 576 323 have proposed the use of liquid ionic complexes which are formed by aluminium halides with certain quaternary ammonium halides or with certain amine hydrohalides, possibly with copper, to catalyse the paraffinic alkylation reaction. Such complexes, known as "molten salts", have been described by C. H. Hussey in *"Advances in Molten Salts Chemistry"*, vol. 5, p. 185, Elsevier, New York, 1985, and by C. A. Angell and J. W. Shuppert in J. Phys. Chem. 84, 538, 1980. Such catalysts are particularly simple to use.

SUMMARY OF THE INVENTION

We have now discovered that the addition of at least one group IVB metal compound, in particular at least one group IVB metal halide, to one of the above salts, constituted by at least one aluminium halide and at least one quatenary ammonium halide and/or at least one amine hydrohalide, improves the reactivity of the catalyst and can enable the alkylation of low reactivity olefins with paraffins to be carried out with good conversions.

More precisely, in one aspect the invention provides a catalytic composition comprising at least one aluminium halide, at least one quaternary ammonium halide and/or at least one amine hydrohalide and at least one group IVB metal compound. In a further aspect, the invention provides a process for alkylation of at least one isoparaffin by at least one olefin, in which the paraffins and olefins are brought into contact with the catalytic composition and the olefins are preferably selected from low reactivity olefins such as ethylene.

The aluminium halide for use in the present invention is preferably selected from the group formed by aluminium chloride and aluminium bromide.

The quatenary ammonium halide for use in the invention has already been described in French patent application FR-A-2 626 572, a description of which is repeated below. Thus the quaternary ammonium halide, which is acyclic or forms part of a cycle, has one of the following general formulae:

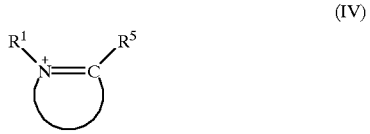

where $R^1$, $R^2$, $R^3$, $R^4$ or $R^5$, which may be identical or different, each represent hydrocarbyl residues generally containing 1 to 12 carbon atoms, for example alkyl, cycloalkyl, aryl, or aralkyl, $R^5$ also possibly being hydrogen or substituted hydrocarbyl residues containing at least one other atom such as nitrogen. Radicals such as $R^6$ may unite two of the above molecules to form, for example, $R^1 R^2 N^+$=$CR^3$—$R^6$—$CR^3$=$N^+R^1R^2(_{31})_2$, $R^6$ possibly being an alkylene residue or a phenylene residue. Cyclic compounds III and IV are constituted by 4 to 10 atoms, preferably 5 to 6 atoms which, in addition to the nitrogen of the quaternary ammonium, may contain carbon atoms or optionally other nitrogen atoms, generally 1 or 2.

The following radicals constitute examples of groups $R^1$, $R^2$, $R^3$, $R^4$ or $R^5$: methyl, ethyl, propyl, isopropyl, butyl, secondary butyl, tertiary butyl, amyl, methylene, ethylidene, phenyl or benzyl; $R^6$ could be a methylene, ethylene, propylene or phenylene group.

In these formulae X represents a halide ion, preferably selected from the group formed by the bromide ion and the chloride ion.

The quaternary ammonium halide for use in the present invention is preferably selected from the group formed by imidazolium and pyridinium salts, preferred examples being N-butylpyridinium chloride, ethylpyridinium bromide, 3-butyl-1-methyl imidazolium chloride, diethylpyrazolium chloride and 3-ethyl-1-methyl imidazolium chloride.

The amine hydrohalides are preferably selected from the group formed by amine hydrochlorides and hydrobromides. More particularly, the amine hydrohalides are selected from the group formed by amine hydrohalides comprising one or two, preferably one, mole of hydrohalic acid, preferably hydrochloric or hydrobromic acid, per mole of amine. It is also possible to use at least one mixture of at least one amine hydrohalide containing one mole of hydrohalic acid per mole of amine and one containing two moles of hydrohalic acid per mole of amine. The hydrohalide derives from an amine or an acyclic diamine or an amine forming part of a cycle which contains at least one nitrogen atom and which generally has the folloing general formulae:

$$R^1R^2R^3N \quad (I)$$

$$R^1N\!=\!CR^2R^3 \quad (II)$$

(III)

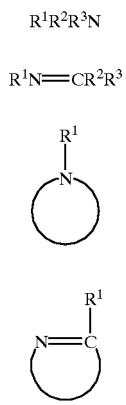

(IV)

where $R^1$, $R^2$ and $R^3$, which may be identical or different, represent hydrocarbyl residues generally containing 1 to 12 carbon atoms, for example alkyl, cycloalkyl, aryl, or aralkyl. One of these substituents $R^1$, $R^2$ or $R^3$ can be hydrogen. Cyclic compounds III and IV are generally constituted by 4 to 10 atoms, preferably 5 to 6 atoms, which, in addition to at least one nitrogen atom, can contain carbon atoms bonded by single or double bonds. Cyclic compounds III and IV can be condensed with other cycles and carry substituents such as amine functions, or fluorine, chlorine or bromine atoms.

The following radicals constitute examples of groups $R^1$, $R^2$ and $R^3$: methyl, ethyl, propyl, isopropyl, butyl, sec-butyl, amyl, methylene, ethylidene, phenyl and benzyl. Cycles such as IV are generally represented by pyridines, imidazoles, triazines, pyrazoles, pyrimidines, and triazoles.

The amine hydrohalide for use in the invention is preferably selected from the group formed by hydrochlorides or hydrobromides of pyridine, 2-, 3- or 4-picolines, lutidines, 2-ethylpyridine, 3-isopropylpyridine, 2-chloro- or 4-chloropyridine, N,N-dimethyl-4-aminopyridine, N-methylimidazole, N-butylimidazole, piperidine and N-methylimidazoline.

The catalytic composition of the invention also comprises, and this constitutes one of the characteristics of the invention, at least one group IVB metal compound, i.e., selected from the group formed by titanium, zirconium and hafnium.

The group IVB metal compound for use in the invention is generally selected from the group formed by an acetate, sulphate, nitrate, perchlorate and the halides. The group IVB metal compound for use in the invention is preferably a halide, which avoids introducing supplemental ions into the reaction medium. More preferably still, the group IVB metal compound for use in the invention is selected from the group formed by zirconium tetrachloride, titanium tetrachloride titanium trichloride, zirconium tetrabromide, titanium tetrabromide, hafnium tetrachloride and hafnium tetrabromide.

The components of the mixtures defined above are preferably used in a molar ratio of aluminium halide to quaternary ammonium halide and/or amine hydrohalide in the range 1.1:1 to 3.5:1, preferably in the range 1.5:1 to 3:1 and in a molar ratio of aluminium halide to group IVB metal halide in the range 1:0.1 to 1:5, preferably in the range 1:0.2 to 1:2.

The compounds in the catalytic composition of the invention can be mixed in any order at a temperature in the range −20° C. to +80° C. The mixture can be formed by simple contact followed by stirring until a liquid or a suspension is formed which can be manipulated. This mixture can be formed outside the alkylation reactor or in the reactor, in the presence or absence of hydrocarbons.

The invention also relates to a catalytic composition comprising, in addition to the mixture of components defined above, at least one slightly basic liquid polar organic compound which is miscible with the component mixture. The organic compound thus generally constitutes the solvent for the components.

Thus the mixture can advantageously be formed in the presence of a liquid polar organic compound which is slightly basic and sufficiently volatile and which is miscible with the component mixture of the mixture and which is then eliminated by evaporation before the catalytic reaction, for example alkylation. The polar organic compound for use in the invention is preferably selected from the group formed by ethers and nitrites, more preferably selected from the group formed by acetonitrile and propionitrile. In this manner, a homogeneous preparation is obtained, (no longer a suspension) which can easily be manipulated.

The invention also relates to a process for alkylating at least one isoparaffin by at least one olefin in the presence of one of the catalytic compositions defined above.

The paraffin for alkylation in the process of the invention is generally selected from the group formed by isobutane, 2-methyl butane, 2-methyl pentane and 3-methyl pentane. The olefin for use in the process of the invention is preferably an olefin with low reactivity such as ethylene.

The catalytic alkylation reaction is generally carried out in a liquid hydrocarbon phase, in a closed system, a semi-open system or a continuous system using one reaction stage as is usual for aliphatic alkylation. The isoparaffin and olefin can be introduced separately or as a mixture. In a continuous or semi-continuous system, the molar ratio between the isoparaffin and the olefin is in the range 2 to 100, for example, advantageously in the range 10 to 50, preferably in the range 5 to 20. In a semi-open system the isoparaffin is introduced first then the olefin, or a mixture of isoparaffin and olefin. Vigorous stirring ensures good contact between the reactants and the catalytic mixture. The reaction temperature can be in the range −40° C. to +70° C., preferably in the range −20° C. to +30° C. The pressure can be in the range from atmospheric pressure to 10 MPa, but will be sufficient to keep the reactants in the liquid phase. The heat generated by the reaction can be eliminated using any of the means known to the skilled person. At the reactor outlet, the hydrocarbon phase is separated from the ionic phase by decanting, then the hydrocarbons are separated by distillation and the starting isoparaffin which has not been converted is recycled to the reactor.

The following examples illustrate the invention without limiting its scope.

Preparation of the Organochloroaluminate 22.9 g of freshly distilled aluminium chloride, 20 ml of heptane and, portionwise, 16.2 g of 1-butyl-3-methyl imidazolium chloride (BMIC) were introduced into a glass flask provided with a magnetic stirrer, purged of air and moisture and kept at 10° C. A liquid composition was obtained.

Alkylation of Isobutane with Ethylene

EXAMPLE 1

6 ml (8.1 g) of the above composition was introduced into a glass reactor kept at 5° C. and intended for the alkylation reaction, to which 2.4 g of anhydrous zirconium tetrachloride (molar ratio $AlCl_3:ZrCl_4:BMIC = 1:0.29:0.54$) was added. A viscous suspension was obtained which could, however, be vigorously stirred using a magnetic bar. 40 g of isobutane and 4 g of butane (internal standard) were introduced into this suspension. The reactor was pressurised to 0.4 MPa. After 6 hours of reaction, 93% of the ethylene had been converted. The reaction product was extracted, and it had the following composition and research and motor octane numbers:

Methylbutane 4.9%
2,3-dimethylbutane 68.1
Other isohexanes 4.2
2,2,4-trimethylpentane 2.7
Other isooctanes 15.4
Higher alkanes 4.7
RON: 98.9
MON: 92.3

The process was repeated several times using the same salt.

EXAMPLE 2

The method of Example 1 was followed but 1.5 g of titanium tetrachloride was added to the chloroaluminate prepared in Example 1 (molar ratio $AlCl_3:TiCl_4:BMIC= 1:0.22:0.54$). After 6 hours of reaction, the ethylene conversion was 95% and the composition of the alkylate formed was as follows:

Methylbutane 7.7%
2,3-dimethylbutane 66.6
Other isohexanes 7.9
2,2,4-trimethylpentane 4.4
Other isooctanes 8.6
Higher alkanes 4.8
RON: 98.6
MON: 92.3

EXAMPLE 3

The method of Example 1 was followed but 1.4 g of titanium trichloride was added to the chloroaluminate prepared in Example 1 (molar ratio $AlCl_3: TiCl_3:BMIC= 1:0.26:0.54$). After 6 hours of reaction, the ethylene conversion was 89% and the composition of the alkylate formed was as follows:

Methylbutane 14%
2,3-dimethylbutane 56.8
Other isohexanes 7.9
2,2,4-trimethylpentane 4.5
Other isooctanes 12.6
Higher alkanes 4.2
RON: 94
MON: 97

COMPARATIVE EXAMPLE 4
(i.e., without group IVB metal halide)

The conditions were identical to those of Example 1, but the zirconium chloride was absent (molar ratio $AlCl_3:BMIC=1:0.54$). After 6 hours of reaction, the ethylene conversion was 60%.

We claim:

1. A catalytic composition consisting essentially of (A) at least one aluminum halide, (B) at least one compound selected from the group consisting of quaternary ammonium halides and amine hydrohalides, and (C) at least one group IVB metal compound, and optionally at least one miscible liquid basic organic polar compound.

2. A catalytic composition according to claim 1, wherein (B) comprises at least one amine hydrohalide.

3. A catalytic composition according to claim 1, wherein (B) comprises at least one quaternary ammonium halide.

4. A catalytic composition according to claim 1, in which the group IVB metal compound is a group IVB metal halide.

5. A catalytic composition according to claim 1, in which the group IVB metal halide is selected from the group consisting of zirconium (IV) chloride and zirconium (IV) bromide, titanium (IV) chloride, titanium (III) chloride, titanium (IV) bromide, titanium (III) bromide, hafnium (IV) chloride, and hafnium (IV) bromide.

6. A catalytic composition according to claim 1, in which the aluminium halide is selected from the group consisting of aluminium chloride and aluminium bromide.

7. A catalytic composition according to claim 1, in which the quaternary ammonium halide is selected from the group consisting of compounds with general formula:

$$R^1R^2R^3R^4N^+ X^-  \quad (I)$$

$$R^1R^2N^+=CR^3R^{4+} X^- \quad (II)$$

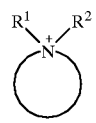
(III)

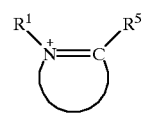
(IV)

where $R^1$, $R^2$, $R^3$ and $R^4$, which may be identical or different, represent hydrocarbyl residues containing 1 to 12 carbon atoms, $R^5$ represents a member selected from the group consisting of a hydrocarbyl residue of 1–12 carbon atoms, hydrogen and substituted hydrocarbyl residues comprising at least one nitrogen atom, cycles III and IV comprising 4 to 10 atoms, and X represents a halide ion.

8. A catalytic composition according to claim 1, in which the quaternary ammonium halide is selected from the group consisting of N-butylpyridinium chloride, ethylpyridinium bromide, 3-butyl-1-methyl imidazolium chloride, diethylpyrazolium chloride and 3-ethyl-1-methyl imidazolium chloride.

9. A catalytic composition according to claim 1, in which the amine hydrohalide is selected from the group consisting of amine hydrohalides containing one mole of hydrohalic acid per mole of amine and amine hydrohalides containing 2 moles of hydrohalic acid per mole of amine.

10. A catalytic composition according to claim 1, in which the amine hydrohalide derives from an amine selected from the group consisting of compounds with general formula:

$$R^1R^2R^3N \quad (I)$$

$$R^1N=CR^2R^3 \quad (II)$$

-continued

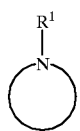

(III)

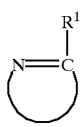

(IV)

where $R^1$, $R^2$, $R^3$, which are identical or different, represent hydrocarbyl residues generally containing to 1 to 12 carbon atoms, and where cycles III and IV comprise by 4 to 10 atoms.

11. A catalytic composition according to claim 1, in which the amine hydrohalide is selected from the group consisting of amine hydrochlorides and amine hydrobromides.

12. A catalytic composition according to claim 1, in which the amine hydrohalide is selected from the group consisting of hydrochlorides and hydrobromides of pyridine, 2-, 3- and 4-picolines, N-methylimidazole, N-butylimidazole, lutidines, 2-ethyl pyridine, 3-isopropylpyridine, 2-chloro- or 4-chloro-pyridine, N,N-dimethyl-4-aminopyridine, piperidine and N-methylimidazoline.

13. A catalytic composition according to claim 4, in which the molar ratio of the aluminium halide to the quaternary ammonium halide and/or amine hydrohalide is in the range 1.1:1 to 3.5:1 and the molar ratio of the aluminium halide to the group IVB metal halide is in the range 1:0.1 to 1:5.

14. A catalytic composition according to claim 1, further consisting essentially of, at least one basic liquid polar organic compound which is miscible with the catalytic composition.

15. A catalytic composition according to claim 14, in which the polar organic compound is selected from the group consisting of acetonitrile and propionitrile.

* * * * *